(12) United States Patent
Peverali et al.

(10) Patent No.: US 6,518,456 B1
(45) Date of Patent: Feb. 11, 2003

(54) PROCESS FOR THE PRODUCTION OF 1-(AMINOMETHYL)-CYCLOHEXYL-ACETIC ACID IN PURE FORM

(75) Inventors: Diego Peverali, Cameri (IT); Mirco Fornaroli, Cameri (IT); Francesco Velardi, Cameri (IT)

(73) Assignee: Procos S.p.A., Cameri (IT)

( * ) Notice: Subject to any disclaimer, the term of this patent is extended or adjusted under 35 U.S.C. 154(b) by 0 days.

(21) Appl. No.: 10/170,629

(22) Filed: Jun. 14, 2002

(30) Foreign Application Priority Data

Dec. 21, 2001 (IT) .......................... MI01A2750

(51) Int. Cl.⁷ ............................... C07C 61/08
(52) U.S. Cl. .................. 562/507; 548/543; 548/558
(58) Field of Search .............. 562/502; 548/543, 548/558

(56) References Cited

U.S. PATENT DOCUMENTS

| | | |
|---|---|---|
| 4,024,175 A | 5/1977 | Satzinger et al. |
| 4,152,326 A | 5/1979 | Hartenstein et al. |
| 5,025,035 A | 6/1991 | Wallace |
| 5,068,413 A | 11/1991 | Steiner et al. |
| 5,084,479 A | 1/1992 | Woodruff |
| 5,091,567 A | 2/1992 | Geibel et al. |
| 5,132,451 A | 7/1992 | Jennings et al. |
| 5,362,883 A | 11/1994 | Jennings et al. |
| 5,510,381 A | 4/1996 | Pande |
| 6,054,482 A | 4/2000 | Augart et al. |
| 6,255,526 B1 | 7/2001 | Pesachovich et al. |

FOREIGN PATENT DOCUMENTS

WO 00/58268 10/2000

*Primary Examiner*—Paul J. Killos
(74) *Attorney, Agent, or Firm*—Young & Thompson

(57) ABSTRACT

A process for the production and purification of gabapentin, i.e. 1-(aminomethyl)cyclohexyl-acetic acid, which comprises hydrolysis of 2-aza-spiro[4.5]decan-3-one with HCl, treatment of the resulting product and filtration with acetone, dissolution in water at isoelectric pH and crystallization or digestion in the hot in mixtures of diisopropyl ether with ethanol or methanol.

8 Claims, No Drawings

PROCESS FOR THE PRODUCTION OF 1-(AMINOMETHYL)-CYCLOHEXYL-ACETIC ACID IN PURE FORM

FIELD OF THE INVENTION

The present invention relates to a process for the preparation and the purification of 1-(aminomethyl)cyclohexyl-acetic acid (gabapentin) (see formula I below), which process overcomes several problems involved in the methods known in patent literature.

Gabapentin is used in the treatment of some cerebral diseases, such as epilepsy, and of diseases typical of the elderly, since it improves brain functionality: see, for example, U.S. Pat. Nos. 5,084,479, 5,025,035, 5,510,381. Furthermore, this medicament has extremely low toxicity ($LD_{50}$>8000 mg/kg).

DISCLOSURE OF THE PRIOR ART

A number of processes for the preparation and purification of gabapentin are known in patent literature, see for instance U.S. Pat. Nos. 4,024,175, 4,152,326, 5,068,413, 6,054,482, 5,091,567, 5,132,451, 5,362,883, 6,255,526, WO 0058268.

Most patents disclose the preparation of gabapentin hydrochloride, from which the free amino acid is obtained by passing an aqueous solution on an anionic resin; gabapentin is subsequently recovered by concentration and precipitation with solvents. These processes involve large volumes and massive amounts of ion exchange resin. On the other hand, an alternative process comprising high-pressure filtration through porous membranes requires specific apparatuses, high pressures and large dilutions. In a further process, the amino acid is freed from its hydrochloride by means of some amines in organic solvents mixtures. Alternative processes involving neither the hydrochloride nor other salts, require however the hydrogenation of intermediates under drastic conditions and can hardly be used on an industrial scale.

DISCLOSURE OF THE INVENTION

The present invention relates to a process for the preparation and purification of Gabapentin of formula (I), 1-(aminomethyl)cyclohexyl-acetic acid), substantially free from the "lactam" of formula (II) (2-Aza-spiro[4.5]decan-3-one) and from inorganic salts.

Said process mainly uses water and small amounts of organic solvents; furthermore, neither ion exchange resins nor the specific industrial apparatuses involved are required.

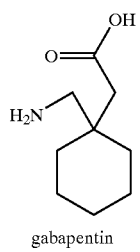

gabapentin
(I)

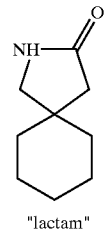

"lactam"
(II)

DETAILED DISCLOSURE OF THE PROCESS

The process of the invention comprises the following steps.

1. Gabapentin hydrochloride is obtained by refluxing 2-aza-spiro[4.5]decan-3-one ("lactam"), for a given time, in a hydrochloric acid aqueous solution. A first crop, obtained upon cooling, is recovered by filtration; the mother liquors are then concentrated to obtain further crops. The recovered product has high purity and contains small amounts of the starting "lactam", moreover the recovery yield is higher than 85%.
2. Crude gabapentin hydrochloride is digested in acetone to remove hydrochloric acid, while further reducing the amount of "lactam" still present. The hemihydrate hydrochloride is obtained after drying.
3. Gabapentin is obtained by treating a hot concentrated aqueous solution of gabapentin hydrochloride with sodium hydroxide to the amino acid isoelectric point, then cooling and filtering the precipitated gabapentin, which is washed with an ethanol/water mixture thereby obtaining a product with sodium chloride content even lower than 1%. The mother liquors are concentrated to obtain further crops, until a 90% overall yield.
4. Gabapentin is crystallized from deionized water, further reducing the content of inorganic salts still present.
5. Crystallization from water is not always necessary, in that sodium chloride concentration can be brought below 0.02% (corresponding to Cl ion≦0.01%) by hot digestion in an ethanol/isopropyl ether or methanol/isopropyl ether mixture. The mixture is then cooled, filtered and dried to obtain almost quantitatively highly pure, anhydrous gabapentin having low content in inorganic salts.

The process of the invention for the preparation of anhydrous gabapentin is a remarkable improvement over the known processes, in that:

1. required reaction times are shorter and procedures are easier, there is no need for ion exchange resins or complex industrial apparatuses for high-pressure filtration through porous membranes, and smaller volumes are necessary per kg of gabapentin obtained.
2. yield is on the average higher than in the known processes involving the acid hydrolysis of the "lactam".

EXAMPLE 1

Gabapentin hydrochloride 150.0 g (0.976 mols) of 2-aza-spiro[4.5]decan-3-one are placed in a 2000 ml round-bottom flask and water (330 ml) is added. The mixture is heated to 60° C., then a 30% hydrochloric acid solution (910 g—7.488 mols) is added in 15 minutes under stirring. Temperature raises from 60° C. to 65° C. during the addition. The mixture is refluxed for 4 hours, then heating is stopped and the mixture is left to cool overnight. After this time, temperature is 23° C. The precipitated product is cooled to 10° C., keeping this temperature for an hour. The product is filtered, washing the filter with acetone.

Wet product: 148.4 g equivalent to 123.7 g of dry product.

($1^{st}$ dry crop analysis—HPLC: 98.58%; 0.70% ("lactam"); chemical titre HClO4: 95.4%; KF: 4.2%).

Molar yield: 58.2%.

Mother liquors (equivalent to 1230.7 g≡1120 ml) are concentrated to about half the volume under atmospheric pressure (560 ml distilled≡615.2 g) then left to cool at room temperature (the product precipitates upon cooling) and further cooled to 10° C., keeping said temperature for an hour. The residue is filtered, washing the filter with acetone.

Wet product: 50.3 g equivalent to 40.0 g of dry product.

($2^{nd}$ dry crop analysis—HPLC: 98.40%; 1.00% ("lactam"); chemical titre HClO4: 94.9%; KF: 4.3%).

Yield: 18.7%.

Mother liquors (equivalent to 557.7 g≡515 ml) are concentrated to about half the volume under atmospheric pressure (260 ml distilled≡285 g), then left to cool at room temperature (the product precipitates upon cooling) and further cooled to 10° C., keeping said temperature for an hour. The residue is filtered, washing the filter with acetone.

Wet product: 25.2 g equivalent to 18.2 g of dry product.

($3^{rd}$ dry crop analysis—HPLC: 98.00%; 1.47% ("lactam"); chemical titre HClO4: 94.5%; KF: 4.3%).

Molar yield: 8.5%.

Total yield: 85.4%.

EXAMPLE 2

Digestion of gabapentin hydrochloride in acetone

Part of the three crops of gabapentin hydrochloride obtained in Example 1 is loaded in a 1000 ml reactor: first wet crop 140 g≡116.7 g (0.539 mols); second wet crop 40 g≡31.8 g (0.147 mols); third wet crop 15 g≡13.0 g (0.060 mols). Acetone (485 ml) is added to the mixture, which is stirred at 40°÷45° C. for an hour, then slowly cooled to room temperature, then further cooled to 10° C., keeping this temperature for an hour. The residue is filtered, washing the residue with acetone (2×30 ml).

Wet product: 162.5 g. The product is dried at 50° C. under vacuum overnight, to obtain 158.8 g of dry product. (Analysis—HPLC: 99.70%; 0.21% ("lactam"); chemical titre HClO4: 95.8%; KF: 4.4%)

Yield: 98.2%.

EXAMPLE 3

Crude gabapentin

Gabapentin hydrochloride hemihydrate (400 g—1.841 mols (Analysis-HPLC: 99.68%; 0.24% ("lactam"); KF: 4.4%; chemical titre: 95.6%) and water (940 ml) are loaded into a 2000 ml glass reactor. The mixture is stirred with heating; the product already dissolves at a temperature of about 23° C. pH is adjusted to 7.1–7.2 by addition of a 30% sodium hydroxide solution (252.1 g) drop by drop. The slightly turbid solution is added with diatomaceous earth (3 g) and stirred for an hour at 60° C. pH is checked and adjusted to constant value of 7.1–7.2 with a 30% sodium hydroxide solution, if needed. The mixture is filtered while hot through fluted filter paper to obtain a clear solution, which is cooled to 15° C., keeping said temperature for an hour. The precipitate is filtered and washed with a water (100 ml)—ethanol (233 ml) mixture cooled to −10° C.

Wet product: 272.4 g. The product is dried at 50° C. under atmospheric pressure for 15 hours, to obtain the dry product: 217.2 g.

(Gabapentin $1^{st}$ crop analysis—HPLC: 99.96%; 0.01% ("lactam"); chemical titre AgNO3: 0.22% (as NaCl) chemical titre HClO4: 94.2%, KF: 6.0%).

Molar yield: 64.9%.

Mother liquors from filtration (1497.4 g) are concentrated under vacuum without exceeding 55° C. inner temperature. After distilling 911.5 g (distillation residue: 586 g), a crystalline white solid precipitates. Most product dissolves upon heating to 75° C., thereby obtaining a slightly turbid solution which is filtered while hot through fluted filter paper and left to crystallize. Precipitation of the product begins at a temperature of about 56° C. The mixture is cooled to 20° C. keeping this temperature for an hour. The residue is filtered, washing with a water (30 ml)—ethanol (70 ml) mixture cooled to −10° C.

Wet product: 107.3 g. The product is dried at 50° C. under atmospheric pressure for 17 hours, to obtain the dry product: 77.4 g.

(Gabapentin $2^{nd}$ crop analysis—HPLC: 99.65%; 0.05% ("lactam"); chemical titre AgNO3: 0.80% (as NaCl) chemical titre HClO4: 98.5%, KF: 0.4%).

Molar yield: 24.1%.

Total yield: 89.0%.

EXAMPLE 4

Crystallized gabapentin base 85.0 g (0.483 mols) of crude gabapentin (Analysis—HPLC: 99.85%; 0.022 ("lactam"); chemical titre AgNO3: 1.00% (as NaCl); chemical titre HClO4: 97.3%; KF: 1.7%), and deionized water (255 g) are loaded into a 500 ml glass reactor. Most product dissolves upon heating to 75° C., thereby obtaining a slightly turbid solution which is filtered while hot through fluted filter paper and left to crystallize. Precipitation of the product begins at a temperature of about 52° C. The product is left to crystallize overnight, then the mixture is cooled to 0°±5° C. keeping said temperature for 1 hour. The mixture is then filtered under vacuum, washing the residue with a cold mixture of deionized water (17 ml)—ethanol (33 ml). The residue is dried in a static dryer under atmospheric pressure at 50° C. overnight.

Dry product: 55.0 g (Analysis—HPLC: 99.93%; 0.07% ("lactam"); chemical titre AgNO3 0.025% (as NaCl), KF 0.08%, chemical titre HClO4 100.3%—IR: form III)

Yield: 66.5%.

Mother liquors from crystallization (250.6 g) are placed in a 1000 ml glass reactor and 58.5 g (0.332 mols) of crude gabapentin (Analysis—HPLC: 99.85%; 0.022% ("lactam"); tit chim. AgNO3 1.00% (as NaCl), chemical titre HClO4: 97.3%; KF 1.7%) and distilled water (31 g) are added. Most product dissolves upon heating to 75° C., thereby obtaining a slightly turbid solution which is filtered while hot through fluted filter paper and left to crystallize. Precipitation of the product begins at a temperature of about 36° C. The product is left to stand overnight, then the mixture is cooled at 0°÷+5° C. keeping this temperature for 1 hour. The mixture is then filtered under vacuum, washing the residue with a cold mixture of distilled water (17 ml)—ethanol (33 ml). The residue is dried in a static dryer under atmospheric pressure at 50° C. overnight.

Dry product: 53.0 g (Analysis—HPLC 99.92%; 0.075% ("lactam"); chemical titre AgNO3: 0.057% (as NaCl); KF: 0.19%; chemical titre HClO4: 99.88%; IR: form III)

Yield: 62.7% (considering the product dissolved in the mother liquors from the first crystallization).

The total yield compared with the starting crude gabapentin, considering the recycle of mother liquors from the first crystallization, is 77.4%.

EXAMPLE 5

Digestion of crystallized gabapentin

Crystallized gabapentin (10.0 g—0.058 mols—Analysis: HPLC: 99.93%; 0.072% ("lactam"); chemical titre AgNO3: 0.041% (as NaCl); KF: 0.13%, chemical titre HClO4: 99.9%), ethanol (27 ml) and isopropyl ether (3 ml) are placed in a 100 ml round-bottom flask, stirring for 4 hours at 50° C. The mixture is cooled to 0°÷+5° C. for 30 minutes, then filtered under vacuum washing the residue with isopropyl ether. The residue is dried in a static dryer under atmospheric pressure at 50° C. for 3 hours, to obtain 9.7 g (Analysis:—HPLC: 99.99%; 0.003% ("lactam"); chemical titre AgNO3: 0.006% (as NaCl), chemical titre HClO4: 99.9%, KF: 0.09%; IR.: form II)

Yield: 97.0%.

EXAMPLE 6

Crude gabapentin

Gabapentin hydrochloride hemihydrate 13.0 kg (59.836 mols) (Analysis—HPLC 99.75%; 0.24% ("lactam"); chemical titre HClO4: 95.6%; KF: 4.4%) and water (30.6 kg) are placed in a 100 l reactor. The mixture is stirred with heating: the product dissolves already at a temperature of about 23° C. pH is adjusted to 7.1–7.2 by gradual addition of a 30% sodium hydroxide solution (8.2 kg). The slightly turbid solution is added with diatomaceous earth (0.1 kg) and kept under stirring for an hour at 50°–55° C. pH is checked and adjusted to constant value of 7.1–7.2 with a 30% sodium hydroxide solution. The mixture is filtered at 60°–65° C. through filter press, the clear solution is collected in a 300 l reactor, which is cooled to 10°–15° C., keeping this temperature for an hour.

The slurry is centrifuged, washing the cake with a water (3.2 kg) and ethanol (5.8 kg) mixture cooled to −10° C. with brine. The mother liquors are collected for further recovery of the second crops.

Wet product 8.8 kg (first crop) equivalent to 6.8 kg of dry product (determined based on the weight loss calculated for a sample dried at 50° C. under atmospheric pressure overnight).

(Analysis—HPLC: 99.99%; 0.005% ("lactam"); chemical titre HClO4: 99.9%; chemical titre AgNO3: 0.06% (as NaCl); KF: 0.08%; IR: Form II).

Molar yield: 66.2%.

The mother liquors (51 kg) of the first crops are placed in a 100 l reactor and distilled under vacuum. 32 kg of water are distilled off without exceeding 55° C. inner temperature, to precipitate a crystalline white solid. Most product dissolves upon heating to 75° C., to obtain a slightly turbid solution, which is filtered while hot through a Fluxa filter, collecting the clear solution in a 300 l reactor. The reactor is cooled to 10°–15° C., keeping said temperature for an hour. The slurry is centrifuged, washing the cake with a water (1 kg) and ethanol (1.8 kg) mixture cooled to −10° C. with brine.

Wet product 3.5 kg (second crop) equivalent to 2.5 kg of dry product (determined based on the weight loss calculated for a sample dried at 50° C. under atmospheric pressure overnight).

(Analysis—HPLC: 99.73%; 0.086% ("lactam"); chemical titre HClO4: 98.3%; chemical titre AgNO3: 1.50% (as NaCl); KF: 0.07%; IR: Form III).

Molar yield: 24.3%.

Overall yield: 90.5%.

EXAMPLE 7

Digestion of gabapentin first crops (ethanol/ether)

3 kg of wet crude gabapentin (first crops of example 6) (equivalent to 2.35 kg of dry product—13.708 mols) are placed in a 15 l round-bottom flask and ethanol (4.9 kg) and isopropyl ether (0.5 kg) are added. The mixture is stirred at 45°–50° C. for 4 hours, then gradually cooled to 0°÷+5° C. After 30 minutes the mixture is filtered by suction, washing the filter cake with isopropyl ether (1 kg), to obtain 2.350 kg of wet product which is dried in a static dryer under atmospheric pressure at 50° C. for 14 hours.

Dry product 2.310 kg (Analysis: HPLC: 99.99%; 0.007% ("lactam"); chemical titre HClO4: 100.5%; chemical titre AgNO3: 0.009% (as NaCl); KF: 0.06%; IR: Form II).

Molar yield: 98.3%.

EXAMPLE 8

Digestion of gabapentin first crops (methanol/ether)

3 kg of wet crude gabapentin (first crops of example 6) (equivalent to 2.35 kg of dry product—13.708 mols) are placed in a 15 l round-bottom flask, and methanol (2.8 kg) and isopropyl ether (3.5 kg) are added. The mixture is stirred at 45°–50° C. for 4 hours, then gradually cooled to 0°÷+5° C. After 30 minutes the mixture is filtered by suction, washing the cake with isopropyl ether (1 kg), to obtain 2.350 kg of wet product which is dried in a static dryer under atmospheric pressure at 50° C. for 14 hours.

Dry product 2.300 kg (Analysis: HPLC: 100%; chemical titre HClO4: 100.2%; chemical titre AgNO3: 0.007% (as NaCl); KF: 0.05%; IR: Form II).

Molar yield: 97.9%.

EXAMPLE 9

Crystallization of Gabapentin second crops 2 kg of wet crude gabapentin (second crops of example 6) (equivalent to 1.4 kg of dry product—8.015 mols) are placed in a 10 l round-bottom flask and deionized water (3.6 kg) is added. Most product dissolves upon heating to 70° C., to obtain a slightly turbid solution, which is filtered while hot through fluted filter paper and left to crystallize. Precipitation of the product starts at a temperature of about 52° C. The product is left to crystallize overnight, then the mixture is cooled to 0°÷+5° C. keeping said temperature for 1 hour. The mixture is then filtered under vacuum, washing the cake with a deionized water (0.29 kg)—ethanol (0.43 kg) mixture cooled at 0°÷+5° C. Washing waters are collected separately from mother liquors, which are recycled for the subsequent crystallization.

1.2 kg of wet product are obtained, equivalent to 0.991 kg of dry product (based on the weight loss calculated for a sample dried at 50° C. under atmospheric pressure overnight).

(Analysis: HPLC: 99.64%; 0.26% ("lactam"); chemical titre HClO4: 99.9%; chemical titre AgNO3: 0.014% (as NaCl); KF: 0.08%; IR: form III).

Molar yield: 70.5%.

The mother liquors from the first crystallization are placed in a 10 l round-bottom flask and 1.4 kg of wet crude gabapentin (second crops of example 6) (equivalent to 1 kg of dry product—5.726 mols) and deionized water (0.45 kg) are added. Most product dissolves upon heating to 75° C., to obtain a slightly turbid solution, which is filtered while hot through fluted filter paper and left to crystallize. Precipitation of the product starts at a temperature of about 36° C. The product is left to crystallize overnight, then the mixture is cooled to 0°÷+5° C. keeping said temperature for 1 hour. The mixture is then filtered under vacuum, washing the cake with a deionized water (0.29 kg) and ethanol (0.43 kg) mixture, cooled at 0°÷+5° C.

Wet product 1.26 kg, equivalent to 0.998 kg of dry product (based on the weight loss calculated for a sample dried at 50° C. under atmospheric pressure overnight).

(Analysis: HPLC: 99.89%; 0.078% ("lactam"); chemical titre HClO4: 99.7%; chemical titre AgNO3: 0.098% (as NaCl); KF: 0.06%; IR: form III).

Molar yield: 70.5%.

The total yield compared with the starting crude gabapentin, considering the recycle of mother liquors from the first crystallization, is 84.1%.

EXAMPLE 10

Digestion of crystallized gabapentin (ethanol/ether)

1.2 kg of wet crystallized gabapentin (first crop of example 9) (equivalent to 0.991 kg of dry product—5.76 mols) and 1.2 kg of wet crystallized gabapentin (second crop of example 9) (equivalent to 0.998 kg of dry product—5.8 mols) are placed in a 10 l round-bottom flask and ethanol (4.14 kg) and isopropyl ether (0.43 kg) are added. The mixture is stirred at 45°–50° C. for 4 hours, then gradually cooled to 0°÷+5° C. After 30 minutes the mixture is filtered by suction, washing the cake with isopropyl ether (1 kg), to obtain 1.99 kg of wet product which is dried in a static dryer under atmospheric pressure at 50° C. for 14 hours.

Dry product 1.91 kg (Analysis—HPLC: 99.99%; 0.003% ("lactam"); chemical titre HClO4: 100.1%; chemical titre AgNO3: 0.013% (as NaCl); KF: 0.05%; IR: form II).

Molar yield: 96.0%.

What is claimed is:

1. A process for the preparation of 1-(aminomethyl) cyclohexyl-acetic acid in pure form, which comprises the following steps:

a) hydrolysis of 2-aza-spiro[4.5]decan-3-one with diluted aqueous HCl and recovery of the resulting 1-(aminomethyl)cyclohexyl-acetic acid hydrochloride by filtration and washing on the filter with acetone;

b) removal of the residual hydrochloric acid from the product obtained in a) by digestion in acetone, filtration and drying;

c) treatment of an aqueous solution of the product obtained in b) with bases to reach the isoelectric point (pH 7.1–7.2), filtration of the resulting 1-(aminomethyl)cyclohexyl-acetic acid and washing on the filter with aqueous ethanol;

d) crystallization of 1-(aminomethyl)cyclohexyl-acetic acid obtained in c) from deionized water; or, alternatively to d)

e) digestion in the hot of 1-(aminomethyl)cyclohexyl-acetic acid obtained in c) in ethanol/diisopropyl ether or methanol/diisopropyl ether and filtration in the cold.

2. A process as claimed in claim 1, wherein step b) is carried out with about 3 parts by volume of acetone per one part by weight of 1-(aminomethyl)cyclohexyl-acetic acid hydrochloride.

3. A process as claimed in claim 1, wherein step b) is carried out at about 40–45° C.

4. A process as claimed in claim 1, wherein step c) is carried out by adding 30% NaOH to a solution of one part by weight of 1-(aminomethyl)cyclohexyl-acetic acid hydrochloride in about 2.4 parts by weight of water.

5. A process as claimed in claim 1, wherein step d) is carried out by crystallization of one part by weight of 1-(aminomethyl)cyclohexyl-acetic acid from about three parts by weight of deionized water.

6. A process as claimed in claim 1, wherein step e) is carried out by digestion of one part by weight of 1-(aminomethyl)cyclohexyl-acetic acid in 2.2–2.4 parts by weight of a mixture of 8.5–10 parts by weight of ethanol and one part by weight of diisopropyl ether.

7. A process as claimed in claim 1, wherein step e) is carried out by digestion of one part by weight of 1-(aminomethyl)cyclohexyl-acetic acid in 2.5–3 parts by weight of a mixture of one part by weight of methanol and 1.3–1.4 parts by weight of diisopropyl ether.

8. A process as claimed in claim 6, characterized in that filtration is carried out at a temperature of 0–5° C.

* * * * *